United States Patent [19]

Wymore

[11] 4,218,401

[45] Aug. 19, 1980

[54] OXYDEHYDROGENATION OF ALCOHOLS

[75] Inventor: C. Elmer Wymore, Midland, Mich.

[73] Assignee: The Dow Chemical Company, Midland, Mich.

[21] Appl. No.: 432,702

[22] Filed: Jan. 11, 1974

[51] Int. Cl.$^2$ .............................................. C07C 45/16
[52] U.S. Cl. ................................... 567/402; 568/471; 568/320; 568/431; 568/432
[58] Field of Search ............... 260/596, 603 R, 590 R, 260/594, 599,

[56] References Cited

U.S. PATENT DOCUMENTS

| 3,080,426 | 3/1963 | Kirshenbaum et al. | 260/596 |
| 3,875,239 | 4/1975 | Stoulhamer et al. | 260/596 |

FOREIGN PATENT DOCUMENTS 823514 11/1959 United Kingdom .................... 260/596

OTHER PUBLICATIONS

Charman, H. B., J. Chem. Soc. (B), 1967, pp. 629-632.
Faith et al. Industrial Chemicals, 2nd Edition, John Wiley & Sons, Inc., N.Y. (1957) pp. 2, 3, 27, 28, 517.

*Primary Examiner*—Norman Morgenstern
*Assistant Examiner*—James H. Reamer
*Attorney, Agent, or Firm*—C. E. Rehberg; Gary R. Plotecher

[57] ABSTRACT

Primary and secondary alcohols are oxidized to aldehydes and ketones, respectively, by passing a gaseous mixture of the alcohol and oxygen (air) over a supported catalyst of Ru, Rh, Pd, Pt, Ir or Os. The catalyst is improved by admixture with a tin compound. The support for the catalyst is preferably alumina, silicon carbide or other inert material having a low surface to weight ratio. Preferred conditions are atmospheric pressure, about 250°-500° C. and a space velocity of 1000-4000/hr. Preferred alcohols are isopropanol, 1-methoxy-2-propanol and ethanol.

10 Claims, No Drawings

OXYDEHYDROGENATION OF ALCOHOLS

BACKGROUND OF THE INVENTION

The use of rhodium salts and of rhodium-tin salt complexes as homogeneous catalysts for the dehydrogenation of isopropanol to make acetone in the absence of oxygen has been reported by H. B. Charman, Nature, 212, 278 (1966) and J. Chem. Soc. (B) 1967, 629.

SUMMARY OF THE INVENTION

Primary and secondary alcohols are oxydehydrogenated to aldehydes and ketones, respectively, by contacting their vapors, in admixture with oxygen-containing gas, with a supported catalyst comprising Ru, Rh, Pd, Pt, Ir or Os. Optionally, but preferably, the catalyst also contains Sn. Preferred alcohols are the lower alkanols and alkoxyalkanols; i.e., those wherein the alkyl and alkylene moieties contain up to about 4 carbon atoms.

DETAILED DESCRIPTION OF THE INVENTION

The Alcohols

Substantially any primary or secondary alcohol can be oxidized by the process of the invention. Since secondary alcohols are more reactive in the process than the primary alcohols, it is sometimes possible to selectively oxidize secondary hydroxyl groups without affecting primary hydroxyl groups. Suitable alcohols include the alkanols, such as ethanol, isopropanol, n-butanol, sec.- butanol, isobutanol, the pentanols, octanols, etc.; the alkoxyalkanols, such as 2-methoxyethanol, 1-ethoxy-2- propanol, 2-butoxy-3-butanol, 1-isopropoxy-3-chloro-2- propanol, 1-tert.-butoxy-3-methoxy-2-propanol; and the higher homologs thereof; and the halo- and aryl-substituted analogs of the foregoing compounds, e.g., benzyl and phenethyl alcohols, propylene chlorohydrin, glycerol mono- and di-bromohydrins, 2-phenoxyethanol, 2(2-ethoxyethoxy)ethanol and the like.

The Catalysts

The catalysts are conveniently made by impregnating a granular supporting solid with a solution or suspension comprising Ru, Rh, Pd, Pt, Ir or Os and then drying the impregnated material. Heating the catalyst to about 300°–600° C. in air sometimes increases its activity.

The active ingredient used to impregnate the support may be substantially any compound containing one or more of the named elements. As a practical matter, the soluble salts of the common acids are preferred, e.g., the chlorides, bromides, nitrates, acetates, sulfates and the like. These are dissolved in any inert solvent, preferably isopropanol, and the support is then impregnated with the solution and then dried.

The support should be a granular solid but should preferably have low to moderate surface-to-weight ratio, e.g., about 1-8 m.$^2$/g. Although materials of higher surface area can be used, they often show less selectivity for the desired oxydehydrogenation. Instead, they tend more to catalyze generalized oxidation leading to carbon-to-carbon cleavage. This excessive activity of the catalysts can be moderated by dilution of the reactant, particularly by dilution with steam. Among the preferred supports are alumina, silicon carbide, diatomaceous earth, silica gel, titanium dioxide, magnesium silicate and the like.

The support is preferably used in granular form, the optimum size of the granules depending somewhat on the size and shape of the reactor. In small scale operations, granules of about 4-20 mesh size are suitable.

Since the catalytic elements are quite expensive, it is desirable to use a low as loading on the support as will give a satisfactory rate of reaction. Also, since the reaction is highly exothermic, the use of too high a load of active catalyst may result in poor temperature control; i.e., hot spots may develop in a fixed-bed catalyst, resulting in damage to the catalyst and/or excessive production of $CO_2$ or other undesired products. Thus, while loadings of 5% by weight (calculated as metal) have been used satisfactorily, the preferred loading when using the preferred catalyst (Rh) is about 0.01 to 0.1%.

In a preferred embodiment of the invention, the preferred catalytic element, Rh, is complexed with Sn. It is known that when salts of Rh and Sn are mixed, a complex is formed and that this complex catalyzes the dehydrogenation of isopropanol in the absence of oxygen, thus producing acetone (see the Charman publications cited above). While the postulated atomic ratio of Sn to Rh is 2:1, a ratio of about 3:1 is preferred in the present invention, though ratios of about 1:1 to 6:1 have been used advantageously.

Reaction Conditions

The most convenient manner of carrying out the invention comprises passing the gaseous reactants over a fixed bed of the supported catalyst. This is most conveniently done at atmospheric pressure, though higher or lower pressure can be used if desired.

Since the reaction is highly exothermic, the heat produced must be dissipated to prevent overheating the catalyst. Although the bed must be heated to a minimum temperature (about 225°-250° C. for Rh catalyst) in order to initiate the reaction, the reaction is self-sustaining thereafter. This makes it possible to reduce the heat input to the preheater and/or catalyst bed without unduly inhibiting the reaction.

In general, as the reaction temperature is increased above the minimum required to initiate reaction, the conversion of the alcohol increases while the selectivity for production of aldehyde or ketone decreases. Thus, the reaction temperature may be about 225°-600° C., the preferred range being about 300°-500°.

The flow rate of the gaseous reactants is herein shown as "gas hourly space velocity" (GHSV), and is the hourly space velocity of the entire gas stream (alcohol+$O_2$+diluent, if any), calculated on the catalyst-packed volume of the reactor, ignoring the space occupied by the catalyst and support, the volume of gas being calculated under standard conditions (0° C. and atmospheric pressure).

The flow rate is not critical and can be varied widely with good results; e.g., the GHSV may be as low as about 100 or as high as 10,000 or more, the preferred range being about 1000-4000.

The elemental oxygen used in the process is preferably supplied as air. It may be further diluted with nitrogen, argon, steam or other inert diluent, or pure oxygen can be used with any such diluents. The theoretically required oxygen is 0.5 mole per alcoholic OH group to be oxidized and it is usually preferred to use approximately this ratio, e.g., 0.45-0.80 mole of $O_2$ per OH group. Substantially lower ratios result in lowered conversion of the alcohol while higher ones result in high conversions but somewhat decreased yields.

The practice of the invention is illustrated by the following examples.

Catalyst Preparation

One drop of concentrated hydrochloric acid, 24 mg. of hydrated $RhCl_3$ containing 41.68% of Rh and 34.6 mg. of $SnCl_2.2H_2O$ were added to a few ml. of isopropanol and the mixture was warmed until the salts were dissolved. The volume was then made up to 40 ml. with additional isopropanol and the solution was refluxed for 1 hour. Then 100 g. of granular alumina (Alcoa T-61, 8-14 mesh) was added and the mixture was evaporated to dryness in a rotating vacuum drier. The catalyst was further dried at 110° C. and then heated in air at 400° C. for 30 minutes. The catalyst had a loading of 0.01% Rh by weight and the atomic ratio Sn/Rh was 3/1. Catalysts having other loadings and supports were prepared similarly.

Reactor

The reactor comprised a ⅝" (15.9 mm.) i.d. Pyrex glass tube 30.6 cm. long having a central thermowell. About 12 ml. of catalyst was packed in the center of the reactor, the ends being packed with silicon carbide granules (grit #10). Thermocouples were placed at the top and center of the catalyst bed and the temperatures reported are the higher of the two readings (usually that at the top). The upper section of carbide packing was heated sufficiently to vaporize the alcohol, thus serving as a preheater.

The alcohol, oxygen and diluent gas were fed into the top of the vertically mounted reactor and the effluent stream from the bottom was analyzed by vapor phase chromatography. When the process was operating effectively a sharp exotherm was shown by the thermocouple at the top of the catalyst bed, its temperature usually rising to a point 100° or more above that in the center of the catalyst bed only about 4 cm. below. Because of this exotherm, the temperature in the reaction zone was highly sensitive to rate of feed, activity of the catalyst and proportion of diluent used in the feed.

Table I summarizes the results of a series of experiments in which isopropanol was oxidized over Sn/Rh catalysts prepared as described above. The catalyst support in Examples 1-11 was a diatomaceous earth of relatively high surface area (8 m.$^2$/g.) and granular size 10-20 mesh, sold under the trade name Chromosorb A, while that of Example 12 was the Alcoa T-61 alumina described above. In the table the gas hourly space velocity as defined above is shown under "GHSV." Results are summarized in Table I.

TABLE I

| | | | Oxidation of Isopropanol (IPA) | | | |
|---|---|---|---|---|---|---|
| Ex. | Cat., Rh Conc., % | GHSV | $N_2:O_2$:IPA Ratio (moles) | Temp., °C. | Conversion, % | Selectivity to Acetone, % |
| 1 | 5 | 2254 | 10.0:0.5:1 | 358 | 100 | 98.4 |
| 2 | 1 | 2426 | 10.0:0.5:1 | 400 | 100 | 86.2 |
| 3 | 0.3 | 2730 | 10.0:0.5:1 | 385 | 97.1 | 86.3 |
| 4 | 0.3 | 5899 | 23.0:0.5:1 | 365 | 97.2 | 90.7 |
| 5 | 0.1 | 2553 | 10.0:0.5:1 | 350 | 100 | 83.5 |
| 6 | 0.1 | 5515 | 23.0:0.5:1 | 350 | 100 | 82.4 |
| 7 | 0.1 | 2553 | 10.0:0.5:1 | 335 | 92.6 | 79.4 |
| 8 | 0.1 | 2553 | 10.0:0.5:1 | 320 | 100 | 82.6 |
| 9 | 0.1 | 2553 | 10.0:0.5:1 | 305 | 91.6 | 84.1 |
| 10 | 0.1 | 2553 | 10.0:0.5:1 | 290 | 94.0 | 85.1 |
| 11 | 0.01 | 2595 | 10.0:0.5:1 | 370 | 89.7 | 81.3 |
| 12 | 0.1 | 1572 | 3.1:0.76:1 | 325 | 93.8 | 94.3 |

In a similar series of experiments, the alcohol to be oxidized was 1-methoxy-2-propanol and the catalyst was Sn/Rh in the atomic ratio 3/1. In Examples 13-21 the support was Alcoa T-61 alumina, 8-12 mesh, and the loading was 0.1% by weight of Rh. In Examples 22-24 the catalyst and load were the same but the support was #10 grit silicon carbide while in Example 25 the support was Chromosorb A diatomaceous silica, 10-20 mesh, and the loading was 1% Rh. Undiluted air was used in an amount to provide the indicated $O_2$:alcohol ratio. Various proportions of water, as indicated, were added to the alcohol feed. Results are shown in Table II.

TABLE II

| | | Oxidation of 1-Methoxy-2-Propanol (MPr) with Air | | | | |
|---|---|---|---|---|---|---|
| Ex. | GHSV | Molar Ratio, $O_2$:DPM | Wt. % $H_2O$ in Feed | Temp., °C. | Conversion, % | Selectivity to Methoxyacetone, % |
| 13 | 564 | 0.47:1 | 0.2 | 417 | 62.4 | 92.6 |
| 14 | 663 | 0.53:1 | 0.2 | 426 | 69.0 | 90.4 |
| 15 | 938 | 0.92:1 | 0.2 | 465 | 78.4 | 83.2 |
| 16 | 1114 | 1.14:1 | 0.2 | 507 | 87.7 | 75.1 |
| 17 | 1591 | 0.75:1 | 0.2 | 426 | 69.4 | 85.9 |
| 18 | 1862 | 0.99:1 | 0.2 | 455 | 85.3 | 85.7 |
| 19 | 2843 | 1.03:1 | 0.2 | 542 | 86.5 | 85.6 |
| 20 | 2996 | 0.78:1 | 0.2 | 535 | 80.5 | 88.6 |
| 21 | 2996 | 0.78:1 | 1.4 | 540 | 85.5 | 92.0 |
| 22 | 1184 | 0.72:1 | 0.2 | 410 | 75.4 | 91.2 |
| 23 | 1184 | 0.72:1 | 4.7 | 390 | 85.2 | 94.4 |
| 24 | 1001 | 0.57:1 | 17.7 | 410 | 78.1 | 93.9 |
| 25 | 1689 | 0.75:1 | 0.2 | 450 | 94.9 | 80.3 |

In another series of experiments, ethanol was oxidized with undiluted air sufficient to give an $O_2$:ethanol ratio of 0.75:1, the catalyst being Sn/Rh (3/1), 0.3% Rh on the Chromosorb A support. Again, water was used as a diluent in some experiments. Results are shown in Table III.

TABLE III

Oxidation of Ethanol With Air

| Ex. | GHSV | H2O/EtOH Mole Ratio | Temp., °C. | Conversion % | Selectivity to Acetaldehyde, % |
| --- | --- | --- | --- | --- | --- |
| 26 | 3107 | 0 | 490 | 88 | 62 |
| 27 | 3107 | 0 | 550 | 96 | 49 |
| 28 | 3881 | 2 | 425 | 67 | 89 |
| 29 | 3881 | 2 | 475 | 76 | 84 |

In another series of experiments, 1-methoxy-2-propanol was oxidized at 350° C. and a GHSV of 1570, the $N_2:O_2$:alcohol ratio being 3.21:0.78:1. The catalyst support was Alcoa T-61 alumina, 8–12 mesh. The catalyst and loadings were as indicated in Table IV.

TABLE IV

Oxidation of 1-Methoxy-2-Propanol (MPr) With Other Catalysts*

| Ex. | Cat. & Conc. | Sn/M Ratio (Molar) | Conv. of MPr, % | Selectivity, Wt. % to Methoxyacetone |
| --- | --- | --- | --- | --- |
| 30 | 0.1% Rh | 1/1 | 83.1 | 92.3 |
| 31 | 0.1% Rh | 3/1 | 87.0 | 91.7 |
| 32 | 0.1% Rh | 6/1 | 81.9 | 92.1 |
| 33 | 0.1% Ir | 3/1 | 60.7 | 85.2 |
| 34 | 0.1% Ru | 6/1 | 79.7 | 88.8 |
| 35 | 1.0% Pd | 4/1 | 88.3 | 90.0 |

*Supported on alumina (8–12 mesh) (0.04 m.$^2$/g.); 350° C.; GHSV 1570 hr.$^{-1}$; $N_2:O_2$; MPr ratio = 3.21:0.78:1

Several experiments were run to show the activities of Sn and Rh separately as catalysts. The alcohol used was isopropanol, the catalyst support was Chromosorb A diatomaceous silica, on which the loading was 17.4% by weight of Sn or 5% of Rh, both being applied as the chloride as described above. The ratio $N_2:O_2$:alcohol was 10:0.5:1 and the GHSV was 2130 for Sn and 2453 for Rh. Results are shown in Table V.

TABLE V

| Ex. | Catalyst | Temp., °C. | Conv., % | Selectivity to Acetone, % |
| --- | --- | --- | --- | --- |
| 36 | Sn | 255 | 16.0 | 13.0 |
| 37 | Sn | 305 | 63.2 | 83.1 |
| 38 | Sn | 358 | 100 | 71.0 |
| 39 | Sn | 400 | 100 | 53.2 |
| 40 | Rh | 250 | 100 | 100 |
| 41 | Rh | 305 | 100 | 90.1 |
| 42 | Rh | 358 | 100 | 88.9 |
| 43 | Rh | 400 | 100 | 71.4 |

I claim:

1. The process of producing an aldehyde or ketone by the oxydehydrogenation of a primary or secondary alcohol, respectively, comprising contacting a gaseous feed containing elemental oxygen and the alcohol with a supported catalyst consisting essentially of Ru, Rh, Pd, Pt, Ir, Os or a combination thereof at a temperature of about 225°–600° C.

2. The process of claim 1 wherein the alcohol is an alkanol.

3. The process of claim 2 wherein the alcohol is a secondary alkanol.

4. The process of claim 3 wherein the alcohol is isopropanol.

5. The process of claim 1 wherein the alcohol is an alkoxyalkanol.

6. The process of claim 5 wherein the alcohol is a 1-alkoxy-2-propanol.

7. The process of producing an aldehyde or ketone by the oxydehydrogenation of a primary or secondary alcohol, respectively, comprising contacting a gaseous feed containing elemental oxygen and the alcohol with a supported catalyst consisting essentially of Sn and a component selected from the group consisting of Ru, Rh, Pd, Pt, Ir, Os or a combination thereof at a temperature of about 225°–600° C.

8. The process of claim 7 wherein the catalyst consists essentially of Sn and Rh.

9. The process of claim 8 wherein the atomic ratio Sn:Rh is about 1:1 to 6:1.

10. The process of claim 9 wherein the alcohol is 1-methoxy-2-propanol, the oxygen is diluted with nitrogen and steam, the reaction temperature is about 300°–500° C. and the molar ratio of oxygen to alcohol is about 0.45:1 to 0.8:1.

* * * * *